(12) United States Patent
Ernst et al.

(10) Patent No.: US 7,939,027 B2
(45) Date of Patent: May 10, 2011

(54) PROCESS FOR THE SYNTHESIS OF DMAPA

(75) Inventors: Martin Ernst, Heidelberg (DE); Steffen Oehlenschläger, Ludwigshafen (DE); Frank Kuhnke, Ludwigshafen (DE); Karl-Heinz Roβ, Grünstadt (DE); Roland Deeg, Grünstadt (DE); Johann-Peter Melder, Böhl-Iggelheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 12/683,015

(22) Filed: Jan. 6, 2010

(65) Prior Publication Data

US 2010/0105952 A1 Apr. 29, 2010

Related U.S. Application Data

(62) Division of application No. 12/092,684, filed as application No. PCT/EP2006/067952 on Oct. 31, 2006, now Pat. No. 7,723,547.

(30) Foreign Application Priority Data

Nov. 3, 2005 (DE) .......................... 10 2005 052 457

(51) Int. Cl.
*B01J 10/00* (2006.01)
*C07C 209/00* (2006.01)
*B01J 35/02* (2006.01)
*B01J 19/00* (2006.01)
*B01J 8/00* (2006.01)

(52) U.S. Cl. ........ 422/187; 564/490; 564/491; 564/492; 564/493; 422/129; 422/211; 422/600; 422/630

(58) Field of Classification Search .................. 422/129, 422/187–190, 211; 564/490–493
See application file for complete search history.

(56) References Cited

U.S. PATENT DOCUMENTS 3,901,949 A * 8/1975 Shinoda et al. ............... 570/220

(Continued)

FOREIGN PATENT DOCUMENTS

EP 0913388 A1 5/1999
(Continued)

OTHER PUBLICATIONS

Caplus on STN, Acc. No. 1988:131013, Toke et al, HU 42053 A2 (Jun. 29, 1987) (abstract).

*Primary Examiner* — Walter D Griffin
*Assistant Examiner* — Natasha Young
(74) *Attorney, Agent, or Firm* — Connolly Bove Lodge & Hutz LLP

(57) ABSTRACT

The present invention relates to a process for the industrial preparation of a diamine starting from a corresponding alkenyl nitrile comprising at least one C—C double bond, which comprises the steps
  (a) reaction of the alkenyl nitrile with a corresponding monoamine in a first reactor so that the monoamine adds exothermically onto the at least one double bond to form an aminoalkyl nitrile, with the monoamine and water being charged initially and the alkenyl nitrile being fed in;
  (b) evaporation of unreacted alkenyl nitrile and monoamine to increase the concentration of the aminoalkyl nitrile product in the bottoms of the first reactor;
  (c) transfer of the aminoalkyl nitrile bottom product from step (b) to a second reactor;
  (d) batchwise catalytic hydrogenation of the aminoalkyl nitrile transferred in step (c) to the diamine in the second reactor, with each batch being obtained by initially charging a catalyst suitable for the hydrogenation of nitriles to amines and also water, the desired diamine and a base, introducing hydrogen into the second reactor and feeding in the aminoalkyl nitrile transferred in step (c); and
  (e) isolation of the diamine and, if appropriate, repetition of the steps (a) to (e).
The invention further relates to an apparatus for preparing these diamines and the use of the apparatuses. A preferred diamine is 3-dimethylaminopropylamine (DMAPA).

8 Claims, 1 Drawing Sheet

U.S. PATENT DOCUMENTS

Figure 1:
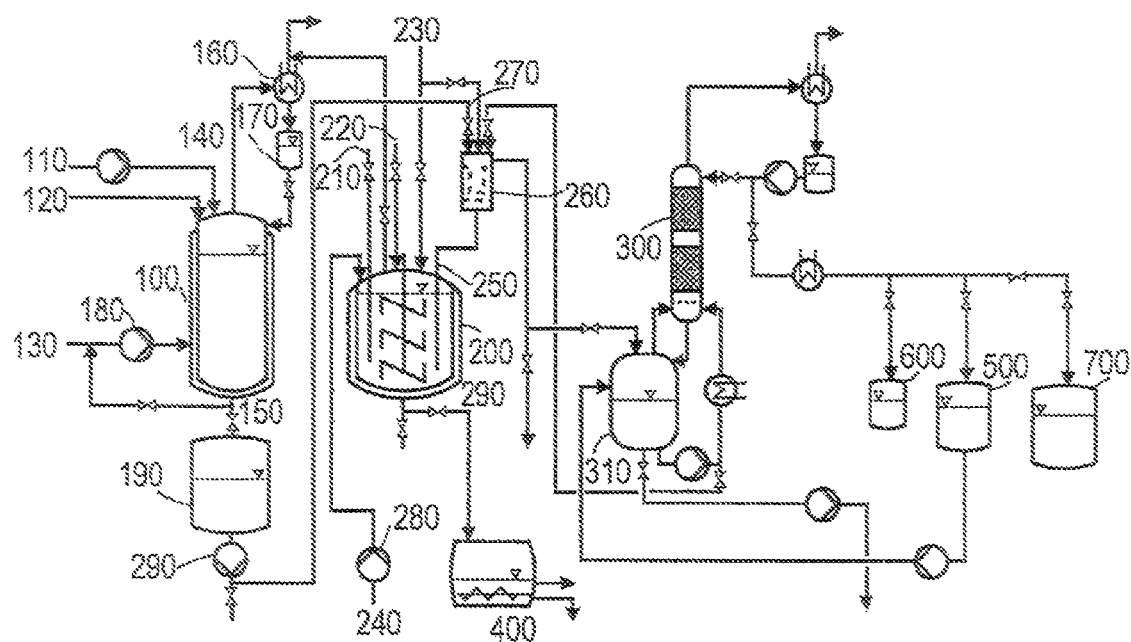

| | | |
|---|---|---|
| 4,172,091 A | 10/1979 | Weber et al. |
| 4,375,003 A | 2/1983 | Allain et al. |
| 4,739,120 A | 4/1988 | Zuckerman |
| 6,660,887 B1 | 12/2003 | Ward et al. |
| 2005/0101797 A1* | 5/2005 | Allgeier .................. 558/459 |

FOREIGN PATENT DOCUMENTS

| | | |
|---|---|---|
| EP | 1 050 527 A2 | 11/2000 |
| JP | 38 21 353 | 10/1963 |
| WO | WO-2004/060039 A2 | 7/2004 |
| WO | WO-2004/060853 A1 | 7/2004 |

* cited by examiner

PROCESS FOR THE SYNTHESIS OF DMAPA

CROSS REFERENCE TO RELATED APPLICATIONS

This application is a divisional of U.S. application Ser. No. 12/092,684 filed May 5, 2008, now U.S. Pat. No. 7,723,547 which is a national stage of PCT/EP2006/067952, filed on Oct. 31, 2006, which claims priority to DE 102005052457.5 filed Nov. 3, 2005, the entire contents of all are hereby incorporated by reference.

The present invention relates to apparatuses and processes for the industrial preparation of a diamine from a corresponding alkenyl nitrile which comprises at least one C—C double bond, and also the use of the apparatuses.

Diamines represent an important chemical group which can be used in a wide variety of ways as starting materials, intermediates or end products. For example, diamines are important building blocks in the synthesis of polyamides and in other polycondensation reactions.

3-Dimethylaminopropylamine (DMAPA, N,N-dimethyl-1,3-diaminopropane) in particular is an important intermediate for the industrial production of, for example, lubricants. In addition, DMAPA serves as starting material for the preparation of coagulants and should itself have anticorrosive properties.

Diamines are, like their amine analogues, frequently prepared by reduction of nitriles. This reaction is particularly advantageous when primary amines are to be obtained.

Thus, for example, WO-A 2004/060853 and WO-A 2004/060039 describe the catalytic hydrogenation of 3-dimethylaminopropionitrile (DMAPN) to DMAPA.

EP-A 0913388 describes the hydrogenation of nitriles for preparing amines with the aid of a cobalt catalyst.

Despite the methods described for the reduction of nitriles to amines or diamines, the question as to how a corresponding nitrile can be made available remains open.

There is therefore a need to provide an integral process which is able to produce diamines from comparatively simple starting materials in a particularly efficient way.

Process which can be used on an industrial scale are of particular importance here, since a simple scale-up from laboratory experiments beyond the pilot plant scale frequently does not lead to the desired results.

It is thus an object of the present invention to provide an industrial process which allows diamines to be prepared in a particularly efficient way.

This object is achieved by a process for the industrial preparation of a diamine starting from a corresponding alkenyl nitrile comprising at least one C—C double bond, which comprises the steps (a) reaction of the alkenyl nitrile with a corresponding monoamine in a first reactor so that the monoamine adds exothermically onto the at least one double bond to form an aminoalkyl nitrile, with the monoamine and water being charged initially and the alkenyl nitrile being fed in;

(b) evaporation of unreacted alkenyl nitrile and monoamine to increase the concentration of the aminoalkyl nitrile product in the bottoms of the first reactor;

(c) transfer of the aminoalkyl nitrile bottom product from step (b) to a second reactor;

(d) batchwise catalytic hydrogenation of the aminoalkyl nitrile transferred in step (c) to the diamine in the second reactor, with the batch being obtained by initially charging a catalyst suitable for the hydrogenation of nitriles to amines and also water, the desired diamine and a base, introducing hydrogen into the second reactor and feeding in the aminoalkyl nitrile transferred in step (c); and (e) isolation of the diamine and, if appropriate, repetition of the steps (a) to (e).

It has been found that an industrial process based on the abovementioned process steps can be used particularly efficiently in terms of yield, selectivity, energy balance, ecological balance and also economic aspects and further important parameters.

The process is based on a two-stage synthesis of a diamine. In the first step, an alkenyl nitrile comprising at least one C—C double bond is reacted with a primary of secondary monoamine in such a way that the amine add onto the C—C double bond. The aminoalkyl nitrile obtained from this reaction is reduced to the desired diamine by means of hydrogen in a further step.

For the purposes of the present invention, the terms "corresponding alkenyl nitrile" and "corresponding monoamine" mean that these compounds are selected so that the diamine having the desired structural formula is obtained after the above-described two synthesis steps.

For example, if the alkenyl nitrile is acrylonitrile (ACN) and the monoamine is dimethylamine (DMA), a reaction of the starting materials to form 3-dimethyl-aminopropionitrile (DMAPN) occurs first. The subsequent hydrogenation gives 3-dimethylaminopropylamine (DMAPA). Expressed in another way, if DMAPA is desired, it can clearly be seen that the corresponding alkenyl nitrile has to be ACN and the corresponding monoamine has to be DMA.

The alkenyl nitrile is preferably a $C_2$-$C_4$-alkene, which may be linear or branched, in which a hydrogen atom is replaced by the cyano group.

The term $C_2$-$C_4$-alkene refers to an alkene having from two to four carbon atoms and comprising at least one C—C double bond. Preference is given to precisely one C—C double bond being present in the $\alpha,\beta$ position relative to the cyano group. Examples of $C_2$-$C_4$-alkenes are ethene, propene, 1-butene, 2-butene, 2-methylpropene.

Examples of nitriles are acrylonitrile, but-2-enenitrile, methacrylonitrile, pent-2-enenitrile, 2-ethylacrylonitrile, 2-methylbut-2-enenitrile and 3-methylbut-2-enenitrile.

Preference is given to ACN.

The monoamine is preferably a primary or secondary amine of the general formula $R^1R^2NH$, where $R^1$, $R^2$ are each, independently of one another, H or $C_1$-$C_4$-alkyl, with the proviso that at least one radical $R^1$, $R^2$ is not hydrogen.

$C_1$-$C_4$-alkyl is methyl, ethyl, n-propyl, i-propyl, 1-n-butyl, 2-n-butyl, i-butyl, t-butyl.

Preference is given to DMA.

If the alkenyl nitrile is ACN and the monoamine is dimethylamine, the desired diamine is DMAPA, which is preferred.

For the purposes of the present invention, the term "industrial preparation" means that the minimum amount used in the reaction of the alkenyl nitrile and in the hydrogenation of the aminoalkyl nitrile is in the order of 100 kg, preferably 1 metric ton.

Step (a) of the process of the invention comprises the reaction of the alkenyl nitrile with a corresponding monoamine in a first reactor so as to exothermically add the monoamine onto the at least one double bond to form an aminoalkyl nitrile, with the monoamine and water being initially charged and the alkenyl nitrile being fed in.

The reaction preferably proceeds in a bubble column.

Furthermore, the monoamine is preferably present in a stoichiometric excess after complete addition of the alkenyl nitrile. Since the monoamine is initially charged and the alkenyl nitrile is added to the reaction mixture, this likewise applies during the entire addition of the alkenyl nitrile. In this way, it can be ensured that the polymerization of the alkenyl nitrile is very largely suppressed. The excess of monoamine relative to alkenyl nitrile is preferably at least 1 mol %, more preferably at least 2.5 mol %, even more preferably at least 5 mol % and particularly preferably at least 10 mol %.

The reaction in step (a) can be carried out at the boiling point and with recirculation of the monoamine. Due to the ascending gas bubbles in the first reactor, better mixing of the reaction mixture can be achieved and heat removal can be effected in a particularly economical way.

For the reaction in step (a) of the process of the invention, both the monoamine, which represents one starting material, and water are initially charged. Here, preference is given to using, based on the monoamine, not more than 20 mol %, more preferably not more than 15 mol % and particularly preferably not more than about 10 mol %, of water.

Owing to the water present, this can serve as intermediate boiler, which aids the removal of the monoamine and its condensation, for example in a reflux condenser. Furthermore, water can serve as catalyst for the addition of the monoamine onto the double bond of the alkenyl nitrile.

The exothermic reaction of the alkenyl nitrile in step (a) can be controlled by carrying out the reaction under reflux of the monoamine. This can, for example, be achieved by means of a reflux condenser. Apart from the monoamine, water also goes into the vapor phase, while the aminoalkyl nitrile formed remains in the bottoms of the first reactor. The reaction is advantageously carried out so that the temperature of the bottoms in step (a) is kept below 130° C., preferably below 120° C., more preferably below 100° C. This applies particularly in the preparation of DMAPA.

Furthermore, it is advantageous for the temperature of the bottoms to remain constant. The temperature of the bottoms is advantageously kept constant and/or below the maximum temperature by means of a temperature-controlled pressure reduction. In particular, this can be achieved in the case of the preparation of DMAPN by reducing the pressure from 5 to 1 bar (gauge pressure).

After all the alkenyl nitrile has been added, the reaction is typically continued in order to complete the conversion.

The process of the invention is particularly suitable as an integral process which encompasses both the reaction of an alkenyl nitrile with a monoamine and the subsequent hydrogenation of the aminoalkyl nitrile intermediate formed. However, the process step of the reaction is itself an advantageous process. Accordingly, a further aspect of the present invention is the above-described step (a) by itself, if appropriate together with the step (b) which is explained in more detail below.

Process step (b) of the process of the invention comprises the evaporation of unreacted alkenyl nitrile and monoamine to increase the concentration of the aminoalkyl nitrile product in the bottoms of the first reactor. After the reaction is complete, the unreacted starting materials have to be removed. This can be achieved by heating the contents of the reactor, with predominantly the monoamine and some of the water evaporating. However, a small proportion of the aminoalkyl nitrile can likewise be present in the vapor phase. Evaporation of the starting materials effects the increase in concentration of the aminoalkyl nitrile product in the bottoms. The constituents separated off by the top of the apparatus, viz. monoamine, water and some aminoalkyl nitrile, can be condensed and at least partly reused for the initial charge for step (a) in a subsequent reaction. To effect this, the condensation is typically temporarily stored in a container.

The aminoalkyl nitrile obtained in this way in the bottoms advantageously has a maximum proportion by weight of monoamine and water of 5% by weight each, preferably not more than 3% by weight each, in particular not more than 2% by weight each.

The aminoalkyl nitrile is then transferred to a second reactor in step (c) of the process of the invention. This can be effected by direct transfer between the reactors connected by means of an appropriate pipe. However, the aminoalkyl nitrile is typically firstly stored temporarily in a storage tank. An advantage of the invention is that the aminoalkyl nitrite intermediate prepared in step (a) of the process of the invention is sufficiently pure for it to be used in the subsequent hydrogenation step. It should merely be necessary to carry out a filtration step in order to separate off solid constituents in an appropriate manner. In one preferred embodiment of the process of the invention, no further purification steps apart from a filtration step are therefore carried out during the transfer of the aminoalkyl nitrite transferred in step (c).

Step (d) of the process of the invention comprises the batchwise catalytic hydrogenation of the aminoalkyl nitrile transferred in step (c) to the diamine in the second reactor, with each batch being obtained by initially charging a catalyst suitable for the hydrogenation of nitriles to amines and also water, the desired diamine and a base, introducing hydrogen into the second reactor and feeding in the aminoalkyl nitrile transferred in step (c).

The process of the invention thus comprises two reaction steps. However, the hydrogenation process described in step (d), if appropriate together with a step for isolating the diamine, is itself also advantageous. A further aspect of the present invention is therefore the batchwise catalytic hydrogenation described in more detail below, if appropriate together with the step of isolation of the diamine.

The diamine obtained in the hydrogenation has to be initially charged in at least small amounts in the hydrogenation in order to ensure a regulated hydrogenation reaction.

In step (d), the catalyst is preferably present in the reaction mixture in an amount of at least 1% by weight, based on the total aminoalkyl nitrile added. The minimum content is preferably 1.25% by weight, more preferably 1.5% by weight. A comparatively high catalyst concentration in the reactor can increase the selectivity and also the life of the catalyst. Based on the mixture charged at the beginning, the proportion of catalyst can be up to 20% by weight, preferably 15% by weight.

The catalyst used for the hydrogenation can in principle be any catalyst suitable for the hydrogenation of nitriles to amines. Such a catalyst can comprise nickel, for example as Raney nickel. Numerous catalysts are known from the prior art. Suitable catalysts are described, for example, in EP-A 913 388, WO-A 2004/060039, WO-A 2004/060853, U.S. Pat. No. 4,739,120, JP-A 38 21 353, U.S. Pat. No. 2,449,035, U.S. Pat. No. 4,375,003, EP-A 1 050 527 and DE 70877.

It is advantageous for the batchwise catalytic hydrogenation in step (d) of the process of the invention to be carried out with an amount of catalyst sufficient for one or more of the subsequent batches being added to the amount of catalyst already present in the second reactor in said step. This means that the total amount of catalyst is not replaced after each batch. In this case, the addition can be carried out at particular intervals, for example after ten batches. However, it is likewise possible for an amount of catalyst to be added after each batch. It is advantageous for the total amount of catalyst to be replaced after a comparatively large number of cycles. Preference is given to complete replacement of the catalyst taking place no earlier than after 50 cycles (execution of steps (a) to (e)). More preferably, a complete replacement of catalyst takes place no earlier than after 100 batches, even more preferably after at least 150 batches.

To carry out the batchwise catalytic hydrogenation in step (d) of the process of the invention, hydrogen is introduced into the second reactor. Furthermore, the aminoalkyl nitrite is added as starting material. The reaction in step (d) is preferably carried out so that a stoichiometric excess of hydrogen is present at any point in time. This stoichiometric excess is preferably at least 5 mol %, more preferably at least 15 mol %, even more preferably at least 20 mol %. The excess of hydrogen can be injected by means of continuous or discontinuous pressure.

In the reaction in step (d) of the process of the invention, a base is used. This base is preferably an alkali metal hydroxide, in particular potassium hydroxide, sodium hydroxide or a mixture thereof.

After the hydrogenation is complete, the isolation of the desired diamine and, if appropriate, repetition of the steps (a) to (e) is carried out as step (e) of the process of the invention.

The isolation of the diamine in step (e) can be achieved by distillation.

It is useful for the reaction product to be filtered and transferred to a distillation column prior to the distillation. It has been found to be advantageous for the major part of the catalyst to be separated off by sedimentation prior to the filtration. Furthermore, it has been found to be advantageous in the distillation for a first fraction consisting mainly of water and monoamine from the distillation to be recirculated to the first reactor. If a first fraction comprises mainly water and the desired diamine, this can be recirculated to the distillation.

The present invention further provides an apparatus for preparing diamines, which comprises
(a) a first reactor for addition of a monoamine onto an alkenyl nitrile, which is provided with at least
  i) one or more separate or joined inlets for the monoamine, the alkenyl nitrile and water;
  ii) at least one first outlet which is suitable for discharging vapor which consists essentially of water and the monoamine from the first reactor; and
  iii) at least one second outlet which is suitable for discharging the aminoalkyl nitrite formed in the bottoms;
(b) a second reactor for the batchwise hydrogenation of the aminoalkyl nitrile, which is provided with at least
  i) at least one first inlet which is connected to the second outlet of the first reactor;
  ii) one or more further separate or joined inlets for hydrogen, catalyst, base, water and an inert gas (preferably nitrogen); and
  iii) an outlet for discharge of the reaction product; and
(c) an apparatus for isolating the diamine from the reaction product, which is provided with at least
  i) at least one inlet which is connected to the outlet of the second reactor, and
  ii) at least one outlet which is suitable for discharging the diamine isolated.

The first outlet of the first reactor is preferably connected to an inlet of an intermediate container which in turn has at least one outlet which makes it possible for the evaporated, if appropriate condensed vapor from the first reactor to be recirculated to this.

Preference is also given to the connection between the first and second reactors comprising a collection vessel and a first filter. However, this is not absolutely necessary.

Preference is likewise given to the second reactor having at least one further outlet for discharging sedimented catalyst or catalyst to be sedimented.

Furthermore, preference is given to the connection between the second reactor and the apparatus for isolating the diamine to have a second filter to stop catalysts from getting into the apparatus for isolating the diamine. The backflushing of the catalyst in the second filter is preferably carried out during the introduction of the aminoalkyl nitrile.

The second filter can be identical to the first filter or both filters can likewise be identical. In the case of only one filter being used, costs can be avoided in this way.

The apparatus for isolating the diamine can, for example, be a distillation column or a rectification column. The distillation column is preferably preceded by a distillation pot so that such a distillation pot is comprised between the connection of the second reactor and the apparatus for isolating the diamine.

The present invention further provides for the use of an apparatus according to the present invention for preparing a diamine by reaction of an alkenyl nitrile with a monoamine and subsequent hydrogenation, preferably using a process according to the invention as has been described above.

The following examples and FIG. 1 illustrate the invention without restricting it. Here, FIG. 1 shows an apparatus according to the invention. The examples relate to the synthesis of DMAPA starting from DMA and ACN.

EXAMPLES

1. DMAPN synthesis 1.1 Procedure in Normal Operation

The synthesis proceeds batchwise in two bubble columns 100 which are operated in parallel and each have a volume of 9.1 m$^3$ and are provided with a reflux condenser 160 (heat transfer area: 75 m$^2$) at 5-1 bar with evaporative cooling and secondary cooling water cooling via a double wall at <100° C. The cooling medium in the condenser 160 is brine ($T_{in}$: −5° C., $T_{out}$: 0° C.), and the secondary cooling water has an inflow temperature of 34° C. and an outflow temperature of 43° C. DMA (2914 kg) via inlet 110 and water (124 kg) via inlet 120 (of which 2727 kg is fresh DMA and 107 kg is fresh water, remainder from intermediate container 170) are initially charged together and ACN (3108 kg) is pumped in via a nozzle from inlet 130 over a period of 2.5 hours. At the entry point, the heat of reaction leads to vaporization of the liquid DMA, which contributes to mixing of the reaction mixture in the bubble column. Vaporized DMA is condensed via outlet 140 in the reflux condenser. During the course of the reaction, the pressure is decreased from 5 to 1 bar by means of a temperature-controlled pressure regulator, so that DMA can be vaporized at constant temperature or below a maximum of 100° C. After injection of the total amount of ACN, the feed pump 180 is switched over to circulation in order to complete the conversion. After a further reaction time of 1 hour, the contents of the reactor are heated via the double wall with 4 bar steam (151° C.), with predominantly DMA and some water and DMAPN (total of 308 kg, of which 204 kg is DMA, 16 kg is water and 88 kg is DMAPN) being vaporized, condensed and temporarily stored in the container 170 until used in the next batch. When the temperature of the bottoms rises to 130° C., the evaporation process is complete. The reactor charge (5942 kg), which still comprises about 1.1% of DMA and 1.8% of water, is cooled and drained via outlet 150 into the storage tank 190.

2. DMAPA Synthesis 2.1 General

The hydrogenation is carried out in two parallel double-wall reactors 200 which each have a volume of 32 m$^3$ and are equipped with a three-stage inclined blade stirrer having a motor power of 120 kW in each case. The cooling medium is secondary cooling water. The batch time is 16 hours and a batch comprises 15 820 kg of crude DMAPN from storage (content: 97.1%).

2.2 Start-Up of the Hydrogenation Reactor with a Fresh Catalyst Charge

Before the first hydrogenation or after total emptying of the vessel, Raney™ Ni catalyst (500 kg as 50% strength suspension in water) and aqueous KOH (60 kg as 25% strength solution) are introduced into the reactor via the pump 280 and the inlet 240 and crude or pure DMAPA (4 m$^3$) is introduced via pump 290 and the initial charge is slurried. The reactor is pressurized twice with nitrogen to 10 bar via inlet 220 and then in each case depressurized to 1 bar. The further procedure is described under 2.3.

2.3 Hydrogenation

Before commencement of the hydrogenation, the reactor is always filled with nitrogen (cf. 2.2 or below). To replace the nitrogen by hydrogen by inlet 210, the reactor is pressurized twice with hydrogen to 10 bar via inlet 210 while stirring and each time depressurized again to 1 bar. After the change of gas from nitrogen to hydrogen, a hydrogen pressure of 10 bar is set. While stirring continually, the catalyst slurry is then heated to 90° C. (double wall, 1 bar steam). When this temperature has been reached, the reactor was pressurised with 30 bar of hydrogen and the metered addition of crude DMAPN from the vessel 190 by means of the pump 290 via the filter 260 and the inlet 250 is commenced. During this, heating is replaced by cooling. The crude DMAPN (15 820 kg) is fed into the catalyst over 9 hours, and further hydrogen is injected with regulation of the pressure. After 9 hours, the hydrogenation is continued for another 1 hour. When hydrogen uptake has ceased, the reactor is depressurized to atmospheric pressure (flare) and stirring is switched off so that the catalyst settles. The contents of the reactor are subsequently pushed via a riser line through the sintered metal filter 260 at 90° C. by means of nitrogen into the distillation pot 310. The contents of the reactor comprise 95.2% of DMAPA. A fill volume of about 5 m$^3$ in which the major part of the catalyst is present is left.

Filtered-off Raney nickel in reactor 200 is rinsed back into the hydrogenation reactor on introduction of the starting materials for the next batch. Before each batch, KOH (6 kg as 25% strength solution in water) is added, and before each 10th batch, additional Raney™ Ni (50 kg as 50% strength suspension in water) and KOH (12 kg as 25% strength aqueous solution) are additionally fed in. In this way, a total amount of about 650 kg of catalyst is reached after 160 batches, corresponding to an initial concentration of about 14%.

The filter 260 is automatically backflushed on introduction of the crude DMAPN, but if necessary can also be flushed with crude DMAPA from the pot 310 or with water from the pipe bridge.

3. Change of Catalyst

After 160 batches (every four months), the catalyst is emptied out completely and the hydrogenation reactor is started up again from the beginning. For this purpose, the contents of the vessel are emptied as usual via the riser line, the vessel is then refilled with 4 m$^3$ of water, stirred, the catalyst is allowed to settle, and the supernatant DMAPA/water washing solution is discharged via the filter 260. This step is repeated three times. The vessel is then flushed two more times, but the washing solution is discharged via the filter into the wastewater. After a total of 5 washing steps, the catalyst is drained via the bottom valve 290 into the settling container 400 where it sediments and is discharged by means of a screw into drums (recycling of the delivery drums). The vessel is flushed again with 5 m$^3$ of water.

The water-comprising washing solution is distilled. The intermediate fraction, which is normally temporarily stored in the container 500 but whose quantity is greatly increased by the water, is not recirculated but instead incinerated or discharged into the wastewater.

4. Distillation

The distillation is a batch distillation in the column 300 at atmospheric pressure and a temperature of the bottoms of from 90 to a maximum of 150° C. The batch time is 16 hours, and a batch comprises 16 500 kg of crude DMAPA. Offgas is taken off first (200 kg, of which 16 kg is NH$_3$, 160 kg is DMA and 24 kg is water), and then low boilers (550 kg, in particular DMA and water) (into container 600), a water-comprising intermediate fraction which goes back into the distillation (into container 500) and the pure fraction comprising 99.5% of DMAPA (15 000 kg) (into container 700) are distilled off and stored in the appropriate containers 500, 600 and 700. 365 kg of DMAPA, 267 kg of bis-DMAPA and 18 kg of DMAPN remain in the bottoms (650 kg) which are incinerated.

The invention claimed is:

1. An apparatus for preparing diamines, which comprises
 (a) a first reactor for addition of a monoamine onto an alkenyl nitrile, which is provided with at least
  i) one or more separate or joined inlets for the monoamine, the alkenyl nitrile and water;
  ii) at least one first outlet which is suitable for discharging vapor which consists essentially of water and the monoamine from the first reactor; and
  iii) at least one second outlet which is suitable for discharging the aminoalkyl nitrile formed in the bottoms;
 (b) a second reactor for the batchwise hydrogenation of the aminoalkyl nitrile, which is provided with at least
  i) at least one first inlet which is connected to the second outlet of the first reactor;
  ii) one or more further separate or joined inlets for hydrogen, catalyst, base, water and an inert gas; and
  iii) an outlet for discharge of the reaction product; and
 (c) an apparatus for isolating the diamine from the reaction product, which is provided with at least
  i) at least one inlet which is connected to the outlet of the second reactor, and
  ii) at least one outlet which is suitable for discharging the diamine isolated,
 wherein the connection between the second reactor and the apparatus for isolating the diamine has a second filter.

2. The apparatus according to claim 1, wherein the first outlet of the first reactor is connected to an inlet of an intermediate container which in turn has at least one outlet which makes it possible for the evaporated, if appropriate condensed vapor from the first reactor to be recirculated to this.

3. The apparatus according to claim 1 wherein the connection between the first and second reactors comprises a collection vessel and a first filter.

4. The apparatus according to claim 1, wherein the second reactor has at least one further outlet via which the sedimented catalyst can be discharged.

5. The apparatus according to claim 3, wherein the first and second filters are identical.

6. The apparatus according to claim 1, wherein the apparatus for isolating the diamine is a distillation column.

7. The apparatus according to claim 1, wherein the distillation column is preceded by a distillation pot.

8. A method of using an apparatus according to claim 1, for preparing a diamine by reaction of an alkenyl nitrile with a monoamine and subsequent hydrogenation.

* * * * *